United States Patent [19]

McIntosh

[11] 4,066,434
[45] Jan. 3, 1978

[54] PLANT GROWTH RETARDANT COMPOSITIONS CONTAINING IMINOCARBONYLPHOSPHONATES AND IMINOCARBONYLPHOSPHONATES

[75] Inventor: Colin Leslie McIntosh, Newark, Del.

[73] Assignee: E. I. Du Pont de Nemours and Company, Wilmington, Del.

[21] Appl. No.: 738,167

[22] Filed: Nov. 2, 1976

Related U.S. Application Data

[63] Continuation-in-part of Ser. No. 621,731, Oct. 15, 1975, abandoned, which is a continuation-in-part of Ser. No. 527,351, Nov. 26, 1974, abandoned.

[51] Int. Cl.$^2$ .......................... A01N 9/36; C07F 9/40
[52] U.S. Cl. ............................................ 71/86; 260/943
[58] Field of Search ............................ 260/943; 71/86

[56] References Cited

U.S. PATENT DOCUMENTS 3,861,898  1/1975  Jelnek .............................. 260/943 X Primary Examiner—Anton H. Sutto

[57] ABSTRACT

Iminocarbonylphosphonates, such as dimethyl 1,1-bis(dimethylamino)methyleneaminocarbonylphosphonate, useful as plant growth retardants.

31 Claims, No Drawings

PLANT GROWTH RETARDANT COMPOSITIONS CONTAINING IMINOCARBONYLPHOSPHONATES AND IMINOCARBONYLPHOSPHONATES

CROSS-REFERENCE TO RELATED APPLICATION

This application is a continuation-in-part of my copending application, U.S. Ser. No. 621,731 filed Oct. 15, 1975, which is a continuation-in-part of U.S. Ser. No. 527,351, filed Nov. 26, 1974, both now abandoned.

BACKGROUND

This invention concerns the discovery that a selected group of iminocarbonylphosphonates are useful for controlling the growth of plants, particularly for preventing bud break and retarding the growth of woody plants.

Bucha and Langsdorf, in pending application Ser. No. 254,670, now U.S. Pat. No. 3,849,102 teaches the use of certain dialkylcarbamoylphosphonates as plant growth retardants. And Langsdorf discloses related compounds also useful as plant growth retardants, such as ammonium ethyl carbamoylphosphonate, in U.S. Pat. No. 3,819,353.

The present invention results from efforts to develop new compounds that could be applied in areas such as power line rights-of-way where low-growing and slow-growing vegatation is especially desirable.

SUMMARY

According to this invention there is provided novel compounds of formula I, processes for making them, formulations containing them, and methods of using them to retard the growth rate of plants.

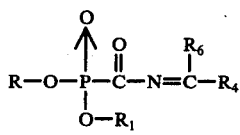

formula I where

R is alkyl of 1 to 4 carbon atoms or benzyl;
$R_1$ is Na, K, $NH_4$, or R;
$R_4$ is $NR_2R_3$, or $OR_5$;
where
$R_2$ is hydrogen or alkyl of 1 to 12 carbon atoms;
$R_3$ is hydrogen or alkyl of 1 to 3 carbon atoms; and
$R_5$ is alkyl of 1 to 3 carbon atoms; and
$R_6$ is $NR_2R_3$, hydrogen, or alkyl of 1 to 3 carbon atoms.

Application of a controlled amount of compound to woody vegetation results in a decrease in the rate of plant growth with little or no apparent damage to the treated plant.

These compounds can also be used to prolong the dormancy of perennial plants. This protects the unsprouted buds from frost damage.

DETAILED DESCRIPTION

Preferred Compounds
Preferred for their higher degrees of biological activity are compounds in which R is methyl or ethyl.

Similarly preferred are compounds in which $R_6$ is $NR_2R_3$ or hydrogen, $R_2$ is hydrogen or methyl, and $R_3$ is hydrogen or methyl.

More preferred for their outstanding plant growth regulant effect are compound in which:
R is methyl or ethyl;
$R_6$ is $NR_2R_3$ or hydrogen;
$R_2$ is hydrogen or methyl; and
$R_3$ is hydrogen or methyl.

Specifically preferred for superior activity are these compounds:
1. dimethyl 1,1-bis(dimethylamino)-methyleneaminocarbonylphosphonate;
2. methyl 1,1-bis(dimethylamino)methyleneaminocarbonylphosphonate, sodium salt;
3. diethyl 1-dimethylaminomethyleneaminocarbonylphosphonate;
4. ethyl 1-dimethylaminomethyleneaminocarbonylphosphonate, sodium salt;
5. dimethyl 1-amino-1-methoxymethyleneaminocarbonylphosphonate;
6. methyl 1-amino-1-methoxymethyleneaminocarbonylphosphonate, sodium salt.

Synthesis

Dialkyl alkoxycarbonylphosphonates are prepared as taught in the literature: Nylen, Ber. 57B, 1023 (1924).

The compounds of this invention can be prepared by refluxing an alkoxycarbonylphosphonate and an alkyl imine in a suitable solvent for one hour and removing the solvent under pressure to yield the iminocarbonylphosphonate.

The sodium salts of these compounds can be prepared by refluxing the dialkyl ester of the iminocarbonylphosphonate and sodium iodide in a suitable solvent for onehalf hour, cooling the mixture, then filtering and drying the precipitate.

Potassium and ammonium salts of these compounds can be prepared from the sodium salts by using the appropriate ion-exchange methods.

The compounds of this invention can also be prepared by refluxing a carbamoylphosphonate and an amide acetal in a suitable solvent, and removing the solvent under reduced pressure to give the iminocarbonylphosphonate.

The preparation of these compounds is further illustrated by the following examples. Parts are by weight unless otherwise specified.

EXAMPLE 1

A solution of 54 parts of dimethyl methoxycarbonylphosphonate and 38 parts of 1,1,3,3-tetramethylguanidine in 1000 parts of anhydrous tetrahydrofuran was refluxed for one hour. The solvent was removed under reduced pressure to yield 77 parts of dimethyl 1,1-bis(-dimethylamino)-methyleneaminocarbonylphosphonate, $n_D^{27} = 1.4855$.

EXAMPLE 2

A solution of 54 parts of dimethyl methoxycarbonylphosphonate and 33 parts of 1,1,3-trimethylguanidine in 1000 parts of anhydrous tetrahydrofuran was refluxed for one hour. The solvent was removed under reduced pressure to yield 71 parts of dimethyl 1-dimethylamino-1-methylaminomethyleneaminocarbonylphosphonate, $n_D^{25} = 1.4989$.

In a similar manner, starting with the appropriate alkoxycarbonylphosphonate and imino compounds, compounds of the following formula can be prepared:

$$\begin{array}{c}
\text{RO} \diagdown \overset{\overset{\displaystyle O}{\uparrow}}{P} - \overset{\overset{\displaystyle O}{\|}}{C} - N = C \diagup \overset{\displaystyle NR_2R_3}{R_4} \\
R_1O \diagup
\end{array}$$

| R | $R_1$ | $R_2$ | $R_3$ | $R_4$ | $N_D^{24}$ |
|---|---|---|---|---|---|
| $CH_3$ | $CH_3$ | $C_{12}H_{25}$ | H | $N(CH_3)_2$ | 1.4631 |
| $C_2H_5$ | $C_2H_5$ | $CH_3$ | $CH_3$ | $N(CH_3)_2$ | |
| $C_4H_9$ | $C_4H_9$ | $CH_3$ | $CH_3$ | $N(CH_3)_2$ | |
| $C_2H_5$ | $C_2H_5$ | H | H | $NH_2$ | |
| $CH_3$ | $CH_3$ | H | H | $NH_2$ | |
| $C_2H_5$ | $C_2H_5$ | $CH_3$ | $CH_3$ | $N(C_2H_5)_2$ | |
| $CH_3$ | $CH_3$ | $CH_3$ | $CH_3$ | $N(C_3H_7)_2$ | |
| ⌬—$CH_2$ | ⌬—$CH_2$ | $CH_3$ | $CH_3$ | $N(CH_3)_2$ | |
| $C_2H_5$ | $C_2H_5$ | $C_3H_7$ | $C_3H_7$ | $NH_2$ | |
| $CH_3$ | $CH_3$ | H | H | $NHC_{12}H_{25}$ | |
| $C_2H_5$ | $C_2H_5$ | H | H | $NHC_{12}H_{25}$ | |

EXAMPLE 3

A solution of 25 parts of dimethyl 1,1-bis(dimethylamino)methyleneaminocarbonylphosphonate and 15 parts of sodium iodide in 300 parts of anhydrous tetrahydrofuran was refluxed for ½ hour. The mixture was then cooled and the precipitate filtered and dried to give 34 parts of methyl 1,1-bis(dimethylamino)methyleneaminocarbonylphosphonate, sodium salt, m.p. 173°.

EXAMPLE 4

A solution of 24 parts of dimethyl 1-dimethylamino 1-methylaminomethyleneaminocarbonylphosphonate and 15 parts of sodium iodide in 300 parts of anhydrous tetrahydrofuran was refluxed for ½ hour. The mixture was then cooled and the precipitate filtered and dried to give 16 parts of methyl 1-dimethylamino-1-methylaminomethyleneaminocarbonylphosphonate, sodium salt, m.p. 181°.

In a similar manner, starting with the appropriate carbonylphosphonate, compounds of the following formula can be prepared:

$$\begin{array}{c}
\text{RO} \diagdown \overset{\overset{\displaystyle O}{\uparrow}}{P} - \overset{\overset{\displaystyle O}{\|}}{C} - N = C \diagup \overset{\displaystyle NR_2R_3}{R_4} \\
R_1O \diagup
\end{array}$$

| R | $R_1$ | $R_2$ | $R_3$ | $R_4$ | $N_D^{24}$ |
|---|---|---|---|---|---|
| $CH_3$ | $Na^+$ | $C_{12}H_{25}$ | H | $N(CH_3)_2$ | 1.5055 |
| $C_2H_5$ | $Na^+$ | $CH_3$ | $CH_3$ | $N(CH_3)_2$ | |
| $C_4H_9$ | $Na^+$ | $CH_3$ | $CH_3$ | $N(CH_3)_2$ | |
| $C_2H_5$ | $Na^+$ | H | H | $NH_2$ | |
| $C_2H_5$ | $Na^+$ | $CH_3$ | $CH_3$ | $N(C_2H_5)_2$ | |
| $CH_3$ | $Na^+$ | $CH_3$ | $CH_3$ | $N(C_3H_7)_2$ | |
| ⌬—$CH_2$ | $Na^+$ | $CH_3$ | $CH_3$ | $N(CH_3)_2$ | |
| $C_2H_5$ | $Na^+$ | $C_3H_7$ | $C_3H_7$ | $NH_2$ | |

By using the appropriate ion exchange methods, the following salts can be prepared from the sodium salts of the corresponding iminocarbonylphosphonate.

| R | $R_1$ | $R_2$ | $R_3$ | $R_4$ |
|---|---|---|---|---|
| $CH_3$ | $K^+$ | H | H | $NH_2$ |
| ⌬—$CH_2$ | $K^+$ | $CH_3$ | $CH_3$ | $N(CH_3)_2$ |
| n-$C_4H_9$ | $NH_4^+$ | H | H | $NH_2$ |
| $CH_3$ | $K^+$ | n-$C_3H_7$ | n-$C_3H_7$ | $N(CH_3)_2$ |
| $C_2H_5$ | $NH_4^+$ | $CH_3$ | $CH_3$ | $N(n-C_3H_7)_2$ |
| $CH_3$ | $K^+$ | $C_{12}H_{25}$ | H | $N(CH_3)_2$ |

EXAMPLE 5

A mixture of 23 parts of 0-methylisourea and 54 parts of dimethyl methoxycarbonylphosphonate in 1000 parts of anhydrous tetrahydrofuran was refluxed for one hour. The solvent was removed to give dimethyl 1-amino-1-methoxy-methyleneaminocarbonylphosphonate, $n_D^{27} = 1.4774$.

In a similar manner, starting with the appropriate carbonylphosphonate and imino compounds, compounds of the following formula can be prepared:

$$\begin{array}{c}
\text{RO} \diagdown \overset{\overset{\displaystyle O}{\uparrow}}{P} - \overset{\overset{\displaystyle O}{\|}}{C} - N = C \diagup \overset{\displaystyle NR_2R_3}{R_4} \\
R_1O \diagup
\end{array}$$

| R | $R_1$ | $R_2$ | $R_3$ | $R_4$ |
|---|---|---|---|---|
| $C_2H_5$ | $C_2H_5$ | H | H | $OCH_3$ |
| ⌬—$CH_2$ | ⌬—$CH_2$ | $CH_3$ | $CH_3$ | $OCH_3$ |
| $CH_3$ | $CH_3$ | n-$C_3H_7$ | n-$C_3H_7$ | $OCH_3$ |
| n-$C_4H_9$ | n-$C_4H_9$ | $CH_3$ | $CH_3$ | $OCH_3$ |
| $CH_3$ | $CH_3$ | $CH_3$ | $C_2H_5$ | $OCH_3$ |
| $CH_3$ | $CH_3$ | $C_{12}H_{25}$ | $CH_3$ | $OCH_3$ |
| $CH_3$ | $CH_3$ | $CH_3$ | $CH_3$ | $OC_3H_7$ |

EXAMPLE 6

A solution of 21 parts dimethyl 1-amino-1-methoxymethyleneaminocarbonylphosphonate and 15 parts of sodium iodide was stirred for 18 hours in 300 parts of anhydrous tetrahydrofuran. The solution is cooled and then filtered to give the methyl 1-amino-1-methoxymethyleneaminocarbonylphosphonate, sodium salt, m.p. 83° d.

In a similar manner compounds of the following formula can be prepared:

$$\begin{array}{c}
\text{RO} \diagdown \overset{\overset{\displaystyle O}{\uparrow}}{P} - \overset{\overset{\displaystyle O}{\|}}{C} - N = C \diagup \overset{\displaystyle NR_2R_3}{R_4} \\
R_1O \diagup
\end{array}$$

| R | $R_1$ | $R_2$ | $R_3$ | $R_4$ |
|---|---|---|---|---|
| ⌬—$CH_2$ | $Na^+$ | $CH_3$ | $CH_3$ | $OC_3H_7$ |
| $CH_3$ | $Na^+$ | n-$C_3H_7$ | n-$C_3H_7$ | $OCH_3$ |
| n-$C_4H_9$ | $Na^+$ | $CH_3$ | $CH_3$ | $OCH_3$ |
| $CH_3$ | $Na^+$ | $CH_3$ | $C_2H_5$ | $OCH_3$ |
| $CH_3$ | $Na^+$ | $C_{12}H_{25}$ | $CH_3$ | $OCH_3$ |

Compounds of the following formula can be made by conventional ion exchange methods, starting with the sodium salts of the corresponding iminocarbonylphosphonates.

$$\begin{array}{c} RO \diagdown \overset{O}{\underset{\|}{P}} \overset{O}{\underset{\|}{-C}} - N = C \diagup \overset{NR_2R_3}{\diagdown R_4} \\ R_1O \diagup \end{array}$$

| R | $R_1$ | $R_2$ | $R_3$ | $R_4$ |
|---|---|---|---|---|
| $CH_3$ | $K^+$ | H | H | $OCH_3$ |
| $CH_3$ | $NH_4^+$ | $CH_3$ | $CH_3$ | $OCH_3$ |
| | $NH_4^+$ | $CH_3$ | $CH_3$ | $OC_3H_7$ |
| C6H5-CH2 | | | | |
| $CH_3$ | $K^+$ | $n-C_3H_7$ | $n-C_3H_7$ | $OCH_3$ |
| $n-C_4H_9$ | $K^+$ | $CH_3$ | $CH_3$ | $OCH_3$ |
| $CH_3$ | $NH_4^+$ | $CH_3$ | $CH_3$ | $OC_3H_7$ |
| $CH_3$ | $K^+$ | $C_{12}H_{25}$ | $CH_3$ | $OCH_3$ |

EXAMPLE 7

A solution of 54 parts of diethyl carbamoylphosphonate and 36 parts of dimethyl formamide dimethyl acetal was refluxed in 1000 parts of anhydrous tetrahydrofuran for eight hours. The solvent was removed under reduced pressure to give 70 parts of diethyl 1-dimethylaminomethyleneaminocarbonylphosphonate, $n_D^{24}$ = 1.4970.

EXAMPLE 8

A solution of 24 parts of diethyl 1-dimethylaminomethyleneaminocarbonylphosphonate plus 17 parts of sodium iodide in 300 parts of anhydrous tetrahydrofuran was refluxed for two hours, cooled, and filtered to give 15 parts of ethyl 1-dimethylaminomethyleneaminocarbonylphosphonate, sodium salt, m.p. 174° d.

EXAMPLE 9

A solution of 98 parts of diethyl methoxycarbonylphosphonate plus 47 parts of acetamidine hydrochloride in 1000 parts of anhydrous tetrahydrofuran can be refluxed for 8 hours and the solvent then removed under reduced pressure to give diethyl 1-amino-1-methylmethyleneaminocarbonylphosphonate. In a similar manner, starting with the appropriate alkoxycarbonylphosphonate and imino compounds, the following compounds can be prepared:

$$\begin{array}{c} RO \diagdown \overset{O}{\underset{\|}{P}} \overset{O}{\underset{\|}{-C}} - N = C \diagup \overset{R_6}{\diagdown R_4} \\ R_1O \diagup \end{array}$$

| R | $R_1$ | $R_4$ | $R_6$ |
|---|---|---|---|
| $C_2H_5$ | $C_2H_5$ | $OCH_3$ | $CH_3$ |
| | | $NH_2$ | $CH_3$ |
| C6H5-CH2 | C6H5-CH2 | | |
| $C_4H_9$ | $C_4H_9$ | $NH_2$ | $CH_3$ |
| $CH_3$ | $CH_3$ | $NH_2$ | $C_3H_7$ |
| $C_2H_5$ | $C_2H_5$ | $OC_3H_7$ | $CH_3$ |
| $CH_3$ | $CH_3$ | $N(CH_3)_2$ | $CH_3$ |
| $CH_3$ | $CH_3$ | $N(CH_3)_2$ | H |
| $C_2H_5$ | $C_2H_5$ | $N(C_3H_7)_2$ | H |
| $CH_3$ | $CH_3$ | $OCH_3$ | H |

EXAMPLE 10

A solution of 22 parts of diethyl 1-amino-1-methylmethyleneaminocarbonylphosphonate and 15 parts of sodium iodide can be refluxed in 300 parts of anhydrous tetrahydrofuran for one hour, cooled, and then filtered to give ethyl 1-amino-1-methylmethyleneaminocarbonylphosphonate, sodium salt.

In a similar manner, starting with the appropriate aminocarbonylphosphonate, the following compounds can be prepared:

$$\begin{array}{c} RO \diagdown \overset{O}{\underset{\|}{P}} \overset{O}{\underset{\|}{-C}} - N = C \diagup \overset{R_6}{\diagdown R_4} \\ R_1O \diagup \end{array}$$

| R | $R_1$ | $R_4$ | $R_6$ |
|---|---|---|---|
| $C_2H_5$ | $Na^+$ | $OCH_3$ | $CH_3$ |
| | $Na^+$ | $NH_2$ | $CH_3$ |
| C6H5-CH2 | | | |
| $C_4H_9$ | $Na^+$ | $NH_2$ | $CH_3$ |
| $CH_3$ | $Na^+$ | $NH_2$ | $C_3H_7$ |
| $C_2H_5$ | $Na^+$ | $OC_3H_7$ | $CH_3$ |
| $CH_3$ | $Na^+$ | $N(CH_3)_2$ | $CH_3$ |
| $C_2H_5$ | $Na^+$ | $N(C_3H_7)_2$ | H |
| $CH_3$ | $Na^+$ | $OCH_3$ | H |

Compounds of the following formula can be made by conventional ion exchange methods starting with the sodium salts of the corresponding methyleneaminocarbonylphosphonates:

$$\begin{array}{c} RO \diagdown \overset{O}{\underset{\|}{P}} \overset{O}{\underset{\|}{-C}} - N = C \diagup \overset{R_6}{\diagdown R_4} \\ R_1O \diagup \end{array}$$

| R | $R_1$ | $R_4$ | $R_6$ |
|---|---|---|---|
| $C_2H_5$ | $K^+$ | $OCH_3$ | $CH_3$ |
| | $NH_4^+$ | $NH_2$ | $CH_3$ |
| C6H5-CH2 | | | |
| $C_4H_9$ | $K^+$ | $NH_2$ | $CH_3$ |
| $CH_3$ | $NH_4^+$ | $NH_2$ | $C_3H_7$ |
| $C_2H_5$ | $K^+$ | $OC_3H_7$ | $CH_3$ |
| $CH_3$ | $NH_4^+$ | $N(CH_3)_2$ | $CH_3$ |
| $C_2H_5$ | $NH_4^+$ | $N(C_3H_7)_2$ | H |
| $CH_3$ | $K^+$ | $OCH_3$ | H |

FORMULATION

Useful formultions of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
| --- | --- | --- | --- |
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |

-continued

| | Percent by Weight | | |
|---|---|---|---|
| | Active Ingredient | Diluent(s) | Surfactant(s) |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

J. B. Buchanan, U.S. Pat. No. 3,576,834, Apr. 27, 1971, Col. 5 Line 36 through Col. 7 Line 70 and Ex. 1–4, 17, 106, 123–140.

R. R. Shaffer, U.S. Pat. No. 3,560,616, Feb. 2, 1971, Col. 3 Line 48 through Col. 7 Line 26 and Examples 3–9, 11–18.

E. Somers, "Formulation", Chapter 6 in Torgeson, "Fungicides", Vol. I, Academic Press, New York, 1967.

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley a Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 11

| | Percent |
|---|---|
| Dimethyl 1,1-bis(dimethylamino)methyleneaminocarbonylphosphonate | 20 |
| Blend of oil soluble sulfonates with polyoxyethylene ethers | 6 |
| Isophorone plus inerts in technical | 74 |

The above ingredients are mixed to give a homogeneous solution.

EXAMPLE 12

| | Percent |
|---|---|
| Methyl 1,1-bis(dimethylamino)methyleneaminocarbonylphosphonate, sodium salt | 90 |
| Synthetic fine silica | 2 |
| Magnesium sulfate heptahydrate plus inerts in technical | 8 |

After blending, the above ingredients are hammer milled so that all particles will pass a U.S.S. 50 mesh (297 mm) screen.

EXAMPLE 13

| | Percent |
|---|---|
| Methyl 1,1-bis(dimethylamino)methyleneaminocarbonylphosphonate, sodium salt | 25 |
| Water plus inerts in technical | 75 |

The above ingredients are mixed to yield a homogeneous solution.

EXAMPLE 14

| | Percent |
|---|---|
| Diethyl 1-dimethylaminomethyleneaminocarbonylphosphonate | 25 |
| Blend of oil soluble sulfonates and polyoxyethylene ethers | 15 |
| Paraffinic spray oil, such as Sunspray 7N ® | 10 |
| Cyclohexanone plus inerts in technical | 50 |

All of the ingredients, except the paraffinic oil, are stirred together and warmed gently to effect solution. After solution is complete, the oil is added and stirring is continued to give a homogeneous liquid.

EXAMPLE 15

| | Percent |
|---|---|
| Ethyl 1-dimethylaminomethyleneaminocarbonylphosphonate, sodium salt | 90 |
| Sodium dialkylsulfosuccinate | 0.5 |
| Solid condensate of ethylene oxide with base formed by condensing propylene oxide with propylene glycol | 3 |
| Synthetic fine silica plus inerts in technical | 6.5 |

The above ingredients are blended, hammer milled, and then passed through a USS 50 mesh screen.

EXAMPLE 16

|  | Percent |
|---|---|
| Dimethyl 1-amino-1-methoxymethyleneamino-carbonylphosphonate | 33 |
| Blend of oil soluble sulfonates and polyoxyethylene ethers | 10 |
| Xylene plus inerts in technical | 57 |

The ingredients are combined and stirred with gentle warming to speed solution. A fine screen filter is included in the packaging operation, to remove any extraneous undissolved material in the product.

EXAMPLE 17

|  | Percent |
|---|---|
| Methyl 1-amino-1-methoxymethyleneamino-carbonylphosphonate, sodium salt | 20 |
| Blend of polyethoxyalcohols | 4 |
| Methanol | 36 |
| Water plus inerts in technical | 40 |

The ingredients are stirred together and warmed gently to effect solution. Extraneous insolubles are removed by passing the solution through a fine screen or cloth filter.

Use

This invention is based on the discovery that the compounds of formula I are effective in modifying the growth rate of plants. More particularly they are useful as plant growth retardants. The term "plant growth retardant" as used in this disclosure means an agent which will slow the growth of a plant and prevent bud break in the spring when applied to the plant or its locus.

The compounds of this invention are especially useful for preventing bud break and retarding the growth of woody plants. They, therefore, can be applied in areas such as power line rights-of-way where controlled vegetation is required. Treatment with these compounds greatly reduces the growth of the trees and shrubs which effectively increases the time until the next trimming is required to keep the trees from growing into the power lines. This can result in a substantial savings in expenditures for powerline maintenance.

These compounds are also effective for retarding the growth rate of viney plants, such as bindweed and morningglory.

These compounds can also be used to prolong the dormancy of perennial plants. This protects the unsprouted buds from frost damage. This delaying action can be especially important in the protection of flower buds, which in some years may sprout early and be killed by cold temperatures. Application to plants during the stage when the following year's buds are forming or developing produces marked retardation of bud break the following spring and greatly reduced growth.

These compounds can be employed as foliar sprays or soil applications. Preferably they are applied as foliar or dormant wood sprays to the point of run-off although lower-volume application can also be effective. They are very versatile and can be applied during different time periods to suit the convenience of the person applying them. For example, they may be applied in spring a short time before the period when maximum plant growth is expected or later in the growing season just after trimming to cause growth retardation. They can also be applied when the year's growth has ceased (late summer, fall, or winter) with the result that treated plants will remain dormant the following spring, while untreated plants will sprout and grow.

The application rate is dependent on the species to be treated and the results desired. In general, rates of 0.25 to 20 kilograms per hectare are used although higher or lower rates can sometimes achieve the desired effect.

To illustrate the growth retardant activity of the compounds and salts of this invention, the following data are presented.

The compounds used in these tests are represented in the tables by the following letter designations.

A = dimethyl 1,1-bis(dimethylamino)methyleneaminocarbonylphosphonate;

B = methyl 1,1-bis(dimethylamino)methyleneaminocarbonylphosphonate, sodium salt;

C = dimethyl 1-dimethylamino-1-methylaminomethyleneaminocarbonylphosphonate;

D = methyl 1-dimethylamino-1-methylaminomethyleneaminocarbonylphosphonate, sodium salt;

E = diethyl 1-dimethylaminomethyleneaminocarbonylphosphonate;

F = ethyl 1-dimethylaminomethyleneaminocarbonylphosphonate, sodium salt, m.p. 174° (dec); G = di- G = dimethyl 1-amino-1-methoxymethyleneaminocarbonylphosphonate;

H = methyl 1-amino-1-methoxymethyleneaminocarbonylphosphonate, sodium salt, m.p. 83° (dec);

I = dimethyl 1-dimethylamino-1-dodecylaminomethyleneaminocarbonylphosphonate;

J = methyl 1-dimethylamino-1-dodecylaminomethyleneaminocarbonylphosphonate, sodium salt.

BRUSH CONTROL TEST

The test compounds were applied in a non-phytotoxic solvent with a wetting agent and a humectant to pots of privet (*Ligustrum* sp.), willow (*Salix* sp.), Forsythia (*Forsythia* sp.) and apple (*Molus* sp.). The plants were maintained in a greenhouse. Plant response ratings were taken one week and eight weeks after application.

| Compound | Application Rate Kg/Ha | Privet 1 wk | Privet 8 wks | Willow 1 wk | Willow 8 wks | Forsythia 1 wk | Forsythia 8 wks | Apple 1 wk | Apple 8 wks |
|---|---|---|---|---|---|---|---|---|---|
| A | 1 | 0 | 8G | 0 | 0 | 0 | 0 | 0 | 3G 3X |
|   | 4 | 0 | 9G | 0 | 9G 5D 7P | 0 | — | 0 | 10G |
| C | 1 | 0 | 2G | 0 | 0 | 0 | 3G | 0 | 0 |
|   | 4 | 0 | 6G | 0 | 0 | 0 | 0 | 0 | 0 |
| B | 1 | 0 | 2G | 0 | 0 | 0 | 0 | 0 | 0 |
|   | 4 | 3D | 4G | 3B | 8G | 0 | 6G | 0 | 3G 3K |
| D | 1 | 0 | 6G | 0 | — | 0 | 0 | 0 | 0 |
|   | 4 | 0 | 10B | 0 | 0 | 0 | 0 | 0 | 1G |
| I | 1 | 0 | 5G | 2C | 0 | 0 | 0 | 0 | 2X |
|   | 4 | 0 | 8G | 4C | — | 1C | 0 | 0 | 2X |
| J | 1 | 0 | 0 | 2C | 0 | 0 | 0 | 0 | 3X |
|   | 4 | 0 | 6G | 5C | 3G | 0 | 0 | 0 | 1G 5X |
| E | 1 | 0 | 7G | 0 | 0 | 0 | 0 | 0 | 3X |
|   | 4 | 0 | 9G | 0 | 1G | 0 | 0 | 0 | 5X |
| F | 1 | 0 | 6G | 0 | 1G | 0 | 0 | 0 | 0 |
|   | 4 | 0 | 10G | 5P 1D | 9G 5D | 0 | 8G | 1C | 9G |
| G | 1 | 0 | 10G | 0 | 0 | 0 | 0 | 0 | 0 |
|   | 4 | 0 | 8G | 0 | 7G 2D | 0 | 2G | 0 | 9G 3X |
| H | 1 | 0 | 6G | 0 | — | 0 | 0 | 0 | 3H |
|   | 4 | 0 | 9G | 0 | 5G | 0 | — | 0 | 2G 3H |

*"wk." = week(s)

The plant response ratings are composed of a number and a letter. The number describes the extent of the response and ranges from zero to ten with zero representing no response, and ten representing 100% response. The letter describes the type of the response, as explained below:

B — burn
C — chlorosis/necrosis
D — defoliation
G — growth retarded
H — formative effect (malformation or hormone type)
P — terminal bud injury
X — axillary stimulation

BRUSH OVERWINTERING TEST

In early Oct. 1974, the test compounds were applied in non-phytotoxic solvent with a wetting agent and a humectant to pots of white birch (*Betula alba*), Sassafras (*Sassafras albidum* var. Molle), willow (*Salix sp.*), loblolly pine (*Pinus Toeda*), California privet (*Ligustrum ovalifolium*), apple (*Pyrus malus* ev. Rome), forsythia (*Forsythia spectabilis*), and redbud (*Cercis canadensis*). The plants were maintained in a greenhouse for five days and then were moved out of doors to a slathouse where they overwintered and remained until July, 1975, when the plant response ratings in the table below were taken.

sponse. The letter describes the type of the response, as explained below:
C — chlorosis/necrosis
G — growth retarded
P — terminal bud injury
X — axillary stimulation

PLANT RESPONSE TEST

Seeds of crabgrass (*Digitaria sp.*), barnyardgrass (*Echinochloa crusgalli*), wild oats (*Avena fatua*), *Cassia tora*, morningglory (*Ipomoea spp.*), cocklebur (*Xanthium sp.*), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment.

| Compound | Rate, Kg/Ha | White Birch | Sassafras | Willow | Loblolly Pine | California Privet | Apple | Forsythia | Redbud |
|---|---|---|---|---|---|---|---|---|---|
| A | 2 | 7G | 5G | 0 | 0 | 0 | 3G | 0 | 0 |
|  | 8 | 9G 10P | 5X 10P | 5G | 7G 1C | 7G | 9G | 3G | 0 |
| B | 2 | 0 | 0 | 0 | 0 | 0 | 0 | 7G | 0 |
|  | 8 | 7G 10P | 1G | 3C | 0 | 4G 5C | 0 | 6G 10P | 0 |

The plant response ratings are composed of a number and a letter. The number describes the extent of the response and ranges from zero to ten with xero representing no response, and ten representing 100% re- Ratings for compounds tested by this procedure are recorded in the following table.

PRIMARY PLANT RESPONSE TEST
POST EMERGENCE

| Compound | Lb. per Acre | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| A | 2 | 6Y | 8G 5I | 8C | 5G | 3G | 0 | 0 | 0 | 0 | 0 | 7G 2U | 4G | 0 | 1C 5G |
| B | 2 | 7C | 8G 5I | 8G 2C | 5G | 3G | 0 | 0 | 1C | 0 | 0 | 1C 6G | 5G | 0 | 6G 1C |
| D | 2 | 7C | 7G | 7G 1C | 4G | 0 | 0 | 0 | 0 | 0 | 0 | 0 | 4G | 0 | 5G |
| I | 2 | 8G 3H 1B | 9G 2B | 8G 1B | 6G 1B | 0 | 0 | 0 | 1B | 0 | 0 | 2C 5G | 5G 1B | 1B | 6G |
| C 2 | | 5D 1B | 5G 1B | 7G 2B | 5G 1B | 2G | 0 | 0 | 0 | 0 | 0 | 5G 1B | 5G 1B | 1B | 1B |
| E | 2 | 1H | 5H | 5H | 1H | 0 | 0 | 0 | 0 | 0 | 0 | 0 | 1H | 0 | 0 |
|  | 2 | 7C | 8G 2H | 7G 1C | 2H | 1H | 0 | 0 | 0 | 0 | 0 | 7G 2C | 2G | 0 | 6G |
| F | | | | | | | | | | | | | | | |
| G | 2 | 6G 6Y | 6G 1H | 6G 1C | 3G | 0 | 0 | 0 | 0 | 0 | 0 | 6G 2U | 0 | 0 | 0 |
| H | 2 | 0 | 5G | 5G | 0 | 0 | 0 | 0 | 0 | 0 | 0 | 0 | 0 | 0 | 0 |

| Compound | Morning Glory | Cocklebur | Cassia | Nutsedge | PRE-EMERGENCE Crabgrass | Barnyard Grass | Wild Oats | Wheat | Corn | Soybean | Rice | Sorghum |
|---|---|---|---|---|---|---|---|---|---|---|---|---|
| A | 0 | 0 | 0 | 0 | 0 | 0 | 0 | 0 | 0 | 0 | 0 | 0 |
| B | 0 | 0 | 0 | 0 | 0 | 0 | 0 | 0 | 0 | 0 | 0 | 0 |
| D | 0 | 0 | 0 | 0 | 0 | 0 | 0 | 0 | 0 | 0 | 0 | 0 |
| I | 0 | 0 | 0 | 0 | 0 | 0 | 0 | 0 | 0 | 0 | 0 | 0 |
| C | 0 | 0 | 0 | 0 | 0 | 0 | 0 | 0 | 0 | 0 | 0 | 0 |
| E | 2G | 2G | 9C | 0 | 2G | 0 | 0 | 0 | 0 | 0 | 0 | 0 |
| F | 2H | 0 | 4G | 0 | 2G | 5C | 0 | 0 | 2G | 2G | 0 | 5G |
| G | 0 | 0 | 0 | 0 | 0 | 0 | 0 | 0 | 0 | 0 | 0 | 0 |
| H | 0 | 0 | 0 | 0 | 0 | 0 | 0 | 0 | 3G | 0 | 0 | 0 |

The plant response ratings are composed of a number and a letter. The number describes the extent of the response and ranges from zero to ten with zero representing no response, and ten representing 100% response. The letter describes the type of the response, as explained below (Note: "6Y" is an exception to this description, and is identified below):

B — burn
C — chlorosis/necrosis
D — defoliation
E — emergence inhibited
G — growth retarded
H — formative effect (malformation or hormone type)
I — increased chlorophyll
U — unusual pigmentation
6Y — abscised buds or flowers

BEAN GROWTH MODIFIER TEST

The test compounds were applied in a non-phytotoxic solvent with a wetting agent and a humectant to pots of 10-day old Black Valentine (pole) snap beans with the primary leaves fully expanded and 3 ½-week old Tenderette (or Tender Crop) (bush) snap bean plants with the early flower buds barely visible. The plants were maintained in a greenhouse, and plant response ratings were taken 1 and 3 weeks after application. The bush beans were retained and harvest measurements were made about one week later.

| | | Bean Growth Modifier Test | | | | | |
|---|---|---|---|---|---|---|---|
| | | Plant Response | | | | | |
| | | B. Valentine | | Harris Tenderette | | # fruit % of | wt. fruit % of |
| Cp | Kg/Ha | 1 wk | 3 wk | 1 wk | 3 wk | check | check |
| B | 1 | 2G | 2G/6F | 1C/2G | 7Q | 80 | 70 |
|  | ½ | 0 | 0 | 0 | 0 | 80 | 120 |
|  | ¼ | 0 | 0 | 0 | 0 | 100 | 110 |
| G | 2 | 0 | 2G/1H | 0 | 2G | 80 | 40 |
|  | ½ | 0 | 2G | 0 | 0 | 110 | 90 |
|  | ¼ | 0 | 0 | 0 | 0 | 100 | 100 |
| A | 1 | 0 | 7G/2H/1C | 0 | 7Q/1C | 50 | 50 |
|  | ½ | 0 | 0 | 0 | 0 | 90 | 80 |
|  | ¼ | 0 | 0 | 0 | 0 | 80 | 100 |

The plant response ratings are composed of a number and a letter. The number describes the extent of the response and ranges from zero to ten with zero representing no response and ten representing 100% response. The letter describes the type of the response, as explained below (Note: "6F" and "7Q" are exceptions to this description, and are identified below):

C — chlorosis/necrosis
G — growth retarded
H — formative effect (malformation or hormone type)
6F — delayed flowering
7Q — decreased number of fruit

SOYBEAN GROWTH MODIFIER TEST

The test compounds were applied in a non-phytotoxic solvent with a wetting agent and a humectant to pots of 30 cm tall Kent soybean plants at the early flowering stage and with 5–6 trifoliate leaves. The plants were maintained in a greenhouse, and plant response ratings were taken 2, 5 and 10 weeks after application. Following the 10-week ratings, the plants were allowed to mature and dry, after which measurements were taken of the number of pods, number of seeds, and seed weight.

| | | Soybean Test | | | | | | |
|---|---|---|---|---|---|---|---|---|
| Compound | Hg/Ka | Plant Response | | | Pod. No. | Seed No. | Seed Wt. (G) | Growth (cm) |
| | | 2 wk | 5 wk | 10 wk | | | | |
| A | 2 | 1C | 3G, 2C | 2G, 2X | 38 | 58 | 9.8 | 11.3 |
|  | ½ | 0 | 1C | 0 | 49 | 66 | 13.1 | 12.0 |
|  | ¼ | 0 | 0 | 0 | 51 | 70 | 13.8 | 11.3 |
| B | 2 | 0 | 1C | 0 | 45 | 82 | 15.5 | 11.0 |
|  | ½ | 0 | 0 | 0 | 53 | 70 | 13.0 | 12.0 |
|  | ¼ | 0 | 0 | 0 | 51 | 70 | 13.8 | 11.3 |

The plant response ratings are composed of a number and a letter. The number describes the extent of the response and ranges from zero to 10 with zero representing no response, and 10 representing 100% response. The letter describes the type of the response, as explained below:
C — chlorosis/necrosis
G — growth retarded
X — axillary stimulation

I claim:

1. A plant growth retardant composition comprising: (a) at least one of the following: a surfactant, a solid or liquid diluent; and (b) an effective amount of a compound of the formula:

$$R-O-\underset{\underset{O-R_1}{|}}{\overset{\overset{O}{\uparrow}}{P}}-\overset{\overset{O}{\|}}{C}-N=\overset{\overset{R_6}{|}}{C}-R_4$$

where
R is alkyl of 1 to 4 carbon atoms or benzyl;
$R_1$ is Na, K, $NH_4$, or R;
$R_4$ is $NR_2R_3$, or $OR_5$;
where
$R_2$ is hydrogen or alkyl of 1 to 12 carbon atoms;
$R_3$ is hydrogen or alkyl of 1 to 3 carbon atoms; and
$R_5$ is alkyl of 1 to 3 carbon atoms; and
$R_6$ is $NR_2R_3$, hydrogen, or alkyl of 1 to 3 carbon atoms.

2. The composition of claim 1 in which R is methyl or ethyl.

3. The composition of claim 1 in which $R_6$ is $NR_2R_3$ or hydrogen, $R_2$ is hydrogen or methyl, and $R_3$ is hydrogen or methyl.

4. The composition of claim 1 in which
R is methyl or ethyl;
$R_6$ is $NR_2R_3$ or hydrogen;
$R_2$ is hydrogen or methyl; and
$R_3$ is hydrogen or methyl.

5. The composition of claim 4 in which the compound is dimethyl 1,1-bis(dimethylamino)methyleneaminocarbonylphosphonate.

6. The composition of claim 4 in which the compound is methyl 1,1-bis(dimethylamino)methyleneaminocarbonylphosphonate, sodium salt.

7. The composition of claim 4 in which the compound is diethyl 1-dimethylaminomethyleneaminocarbonylphosphonate.

8. The composition of claim 4 in which the compound is ethyl 1-dimethylaminomethyleneaminocarbonylphosphonate, sodium salt.

9. The composition of claim 4 in which the compound is dimethyl 1-amino-1-methoxymethyleneaminocarbonylphosphonate.

10. The composition of claim 4 in which the compound is methyl 1-amino-1-methoxymethyleneaminocarbonylphosphonate, sodium salt.

11. A compound of the formula:

$$R-O-\underset{\underset{O-R_1}{|}}{\overset{\overset{O}{\uparrow}}{P}}-\overset{\overset{O}{\|}}{C}-N=\overset{\overset{R_6}{|}}{C}-R_4$$

where
R is alkyl of 1 to 4 carbon atoms or benzyl;
$R_1$ is Na, K, $NH_4$, or R;
$R_4$ is $NR_2R_3$, or $OR_5$;
where
$R_2$ is hydrogen or alkyl or 1 to 12 carbon atoms;
$R_3$ is hydrogen or alkyl or 1 to 3 carbon atoms; and
$R_5$ is alkyl of 1 to 3 carbon atoms; and
$R_6$ is $NR_2R_3$, hydrogen, or alkyl of 1 to 3 carbon atoms.

12. The compound of claim 11 in which R is methyl or ethyl.

13. The compound of claim 11 in which $R_6$ is $NR_2R_3$ or hydrogen, $R_2$ is hydrogen or methyl, and $R_3$ is hydrogen or methyl.

14. The compound of claim 11 in which:
R is methyl or ethyl;
$R_6$ is $NR_2R_3$ or hydrogen;
$R_2$ is hydrogen or methyl; and
$R_3$ is hydrogen or methyl.

15. The compound of claim 14: dimethyl 1,1-bis(dimethylamino)methyleneaminocarbonylphosphonate.

16. The compound of claim 14: methyl 1,1-bis(dimethylamino)methyleneaminocarbonylphosphonate, sodium salt.

17. The compound of claim 14: diethyl 1-dimethylaminomethyleneaminocarbonylphosphonate.

18. The compound of claim 14: ethyl 1-dimethylaminomethyleneaminocarbonylphosphonate, sodium salt.

19. The compound of claim 14: dimethyl 1-amino-1-methoxymethyleneaminocarbonylphosphonate.

20. The compound of claim 14: methyl 1-amino-1-methoxymethyleneaminocarbonylphosphonate, sodium salt.

21. A method for preventing bud break and retarding the growth rate of plants which comprises applying to the plants an effective amount of a compound of the formula:

$$R-O-\underset{\underset{O-R_1}{|}}{\overset{\overset{O}{\uparrow}}{P}}-\overset{\overset{O}{\|}}{C}-N=\overset{\overset{R_6}{|}}{C}-R_4$$

where
R is alkyl of 1 to 4 carbon atoms or benzyl;
$R_1$ is Na, K, $NH_4$, or R;
$R_4$ is $NR_2R_3$, or $OR_5$;
where
$R_2$ is hydrogen or alkyl of 1 to 12 carbon atoms;
$R_3$ is hydrogen or alkyl of 1 to 3 carbon atoms; and
$R_5$ is alkyl of 1 to 3 carbon atoms; and
$R_6$ is $NR_2R_3$, hydrogen, or alkyl of 1 to 3 carbon atoms.

22. The method of claim 21 in which R is methyl or ethyl.

23. The method of claim 21 in which $R_6$ is $NR_2R_3$ or hydrogen, $R_2$ is hydrogen or methyl, and $R_3$ is hydrogen or methyl.

24. The method of claim 21 in which R is methyl or ethyl; $R_6$ is $NR_2R_3$ or hydrogen; $R_2$ is hydrogen or methyl; and $R_3$ is hydrogen or methyl.

25. The method of claim 24 in which the compound is dimethyl 1,1-bis(dimethylamino)methyleneaminocarbonylphosphonate.

26. The method of claim 24 in which the compound is methyl 1,1-bis(dimethylamino)methyleneaminocarbonylphosphonate, sodium salt.

27. The method of claim 24 in which the compound is diethyl 1-dimethylaminomethyleneaminocarbonylphosphonate.

28. The method of claim 24 in which the compound is ethyl 1-dimethylaminomethyleneaminocarbonylphosphonate, sodium salt.

29. The method of claim 24 in which the compound is dimethyl 1-amino-1-methoxymethyleneaminocarbonylphosphonate.

30. The method of claim 24 in which the compound is methyl 1-amino-1-methoxymethyleneaminocarbonylphosphonate, sodium salt.

31. A method for retarding the growth rate of viney plants which comprises applying to the plants an effective amount of a compound of the formula:

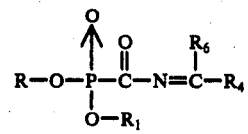

where
R is alkyl of 1 to 4 carbon atoms or benzyl;
$R_1$ is Na, K, $NH_4$, or R;
$R_4$ is $NR_2R_3$, or $OR_5$;
where
$R_2$ is hydrogen or alkyl of 1 to 12 carbon atoms;
$R_3$ is hydrogen or alkyl of 1 to 3 carbon atoms; and
$R_5$ is alkyl of 1 to 3 carbon atoms; and
$R_6$ is $NR_2R_3$, hydrogen, or alkyl of 1 to 3 carbon atoms.

* * * * *